(12) United States Patent
Huang et al.

(10) Patent No.: US 8,323,695 B2
(45) Date of Patent: Dec. 4, 2012

(54) METHOD FOR STABILIZING PHENYLEPHRINE

(75) Inventors: Hugh Huang, Princeton, NJ (US); Jonathan Zeszotarski, Chalfont, PA (US); Anthony Bean, Lansdale, PA (US); William Michael Nichols, Somerset, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 896 days.

(21) Appl. No.: 11/891,693

(22) Filed: Aug. 13, 2007

(65) Prior Publication Data

US 2009/0047343 A1    Feb. 19, 2009

(51) Int. Cl.
*A61K 9/14*   (2006.01)

(52) U.S. Cl. ........................................................ 424/489

(58) Field of Classification Search ............................ None
See application file for complete search history.

(56) References Cited

U.S. PATENT DOCUMENTS

| 4,994,279 | A  | * | 2/1991  | Aoki et al. ............... 424/494 |
| 6,500,463 | B1 | * | 12/2002 | van Lengerich ........... 424/499 |
| 2006/0004094 | A1 |  | 1/2006 | Agisim |
| 2006/0057205 | A1 | * | 3/2006 | Srinivasan et al. ........ 424/472 |
| 2006/0121066 | A1 | * | 6/2006 | Jaeger et al. .............. 424/400 |
| 2006/0127473 | A1 |  | 6/2006 | Nichols |
| 2007/0254031 | A1 | * | 11/2007 | Shimizu et al. ........... 424/468 |
| 2008/0020055 | A1 | * | 1/2008 | Monteith et al. ........... 424/497 |

FOREIGN PATENT DOCUMENTS

| GB | 1084864      |   | 9/1967  |
| JP | 2005-60294 A | * | 3/2005  |
| JP | P200560294   |   | 3/2005  |
| WO | 02/41920     |   | 5/2002  |
| WO | 03/089007    |   | 10/2003 |
| WO | 2005/023236  |   | 3/2005  |
| WO | 2006/067593  |   | 6/2006  |
| WO | 2008/039737  |   | 4/2008  |

* cited by examiner

*Primary Examiner* — Susan Tran
(74) *Attorney, Agent, or Firm* — Evan J. Federman

(57) ABSTRACT

The present invention relates to a process for stabilizing phenylephrine including drying an acidic solution of phenylephrine and pharmaceutical compositions including stabilized phenylephrine.

8 Claims, No Drawings

METHOD FOR STABILIZING PHENYLEPHRINE

FIELD OF THE INVENTION

The present invention relates to a method for stabilizing phenylepherine.

BACKGROUND OF THE INVENTION

It is important for active pharmaceutical ingredients (APIs) to be stable for prolonged periods of time. Generally, at least a two year shelf life is desirable as a raw bulk material or as a finished product or dosage form. Unfortunately, APIs often may not be stable alone or in combination with excipients that are used in dosage formulations such as tablets, capsules, films, etc.

Many API's may be unstable and degrade in the presence of oxygen. Oxygen sensitive API's may be stabilized by several different methods. For instance, the drug product and the API may be processed under inert atmospheres, e.g. under argon or nitrogen gas blankets, however, this requires special manufacturing conditions and adds to the cost of manufacturing a drug product. Antioxidants may be used to help stabilize oxygen sensitive API's. Useful antioxidants include bi-sulfites and ascorbic acid; however, there have been safety issues associated with the use of some antioxidants. In particular, sulfites have been determined to be harmful. Thus, the use of antioxidants is less desirable due to safety issues and it generally costs more than preparing a nasal spray solution under inert conditions.

Phenylephrine is an API used in pharmaceutical compositions as a decongestant. There has been increased use of phenylephrine in cold medications due to restrictions placed on the sale of compositions containing pseudoephedrine. However, phenylephrine is known to be unstable. This instability has been shown both in accelerated conditions of high humidity and temperature, but also in the presence of other incompatible inactive ingredients or active ingredients such as chlorpheniramine maleate. There are several nasal spray formulations for the treatment of nasal decongestion that contain phenylephrine. Marketed nasal sprays containing phenylephrine may be stabilized by manufacturing the spray under inert atmospheres, e.g. under argon or nitrogen gas blankets, which requires special manufacturing conditions and is costly.

US Published Patent Application 2006-0127473 discloses stabilized phenylephrine compositions comprising silicified microcrystalline cellulose.

Japanese Patent Application P2005-62094A discloses stabilized pharmaceutical compositions containing phenylephrine, carbinoxamine and citric acid.

DETAILED DESCRIPTION OF THE INVENTION

The present invention provides a method of making stabilized phenylephrine by drying an acidic solution of phenylephrine. The present invention also provides for pharmaceutical composition including the stabilized phenylephrine. The composition may be stable where the active ingredient(s) experience minimal or no degradation e.g. produces less than 2% degradants when stored at room temperature over a two year period of time. As used herein room temperature conditions are defined as 20-30° Celsius and 60 to 70% relative humidity. Generally, accelerated stability conditions are defined as 40-50° Celsius and 75% relative humidity. The composition may be a tablet including a direct compressed tablet. The phenylephrine used in the present invention may be a derivative or a pharmaceutically acceptable salt thereof, in a pharmaceutically effective amount. In several embodiments, the phenylephrine produces less than 2% degradants when stored at room temperature over a two year period of time. In several embodiments, the solid dosage form may be an immediate release orally digested tablet, an immediate release bucally fast disintegrating tablet, a chewable tablet, a confectionery tablet, an edible film or a sustained release orally ingested tablet. In several embodiments, there is provided a package including the composition. In one embodiment the dosage form contains a combination of phenylephrine hydrochloride and chlorpheniramine maleate. The package may include drug facts. The composition may be positioned in blister containers.

Phenylephrine is known to experience physical and chemical degradation. Degradation of phenylephrine may be caused by a variety of factors including, but not limited to, the presence of oxygen, moisture, reducible sugars, bases, high temperatures, etc. Degradation of phenylephrine is also caused by the combination of phenylephrine with chlorpheniramine maleate which in turn causes the formation of phenylephrine-maleate adducts. Degradation of phenylephrine may be noticed by a change in color, e.g. changing from a whitish color to a darker, blackish color. Additionally, phenylephrine may degrade chemically as recorded by degradation peaks during analysis, such as an HPLC analysis. It is desirable to prevent, reduce or minimize the degradation of phenylephrine. An embodiment of the present invention provides a stable pharmaceutical composition having phenylephrine in a therapeutically effective amount wherein the phenylephrine has been spray dried. An additional embodiment of the present invention provides a stable composition of phenylephrine in a therapeutically effective amount wherein the phenylephrine has been layered or sprayed onto a substrate. Surprisingly, it has been found that spray drying an acidic solution of phenylephrine increases the stability of phenylephrine in solid formulations.

Phenylephrine may be unstable in the presence of active ingredients which are the soluble salts of maleic acid. Phenylephrine-Maleate adducts form when phenylephrine hydrochloride is combined with chlorpheniramine maleate in solution and in solid dosage forms. This is due to the presence of phenylephrine with maleic acid. It was discovered that a pH below 6.0 yields low levels of one type of phenylephrine-maleate adduct (degradant #1) and it was also discovered that a pH above 4.5 yields low levels of a second type of phenylephrine-maleate adduct (degradant #2). Hence, when the two active ingredients are combined, it is desirable to have a pH between 4.5 and 6.0 in a solution.

Useful amounts of phenylephrine include from about 1 milligram to about 60 mg, or from about 1 mg to about 15 mg, or from about 5 mg to about 10 mg. or from about 5 mg to about 10 mg or in an amount from about 5 to about 12 mg. Various salts of phenylephrine may be employed in the present invention including but not limited to phenylephrine hydrochloride, phenylephrine tannate and mixtures thereof.

Various embodiments of the present invention provide compositions with at least two API's. An additional embodiment provides for a composition with three API's, of which at least one API is an oxygen sensitive API. Useful additional API's include, but are not limited to:

(a) antimicrobial agents such as triclosan, cetylpyridium chloride, domiphen bromide, quaternary ammonium salts, zinc compounds, sanguinarine, fluorides, alexidine, octonidine, EDTA, and the like;

(b) non-steroidal anti-inflammatory and pain reducing agents such as aspirin, acetaminophen, ibuprofen, ketoprofen, diflunisal, fenoprofen calcium, flurbiprofen sodium, naproxen, tolmetin sodium, indomethacin, celecoxib, valdecoxib, parecoxib, rofecoxib and related salts and the like;

(c) antitussives such as benzonatate, caramiphen edisylate, menthol, dextromethorphan hydrobromide, chlophedianol hydrochloride and the like;

(d) antihistamines such as brompheniramine maleate, chlorpheniramine maleate, carbinoxamine maleate, cetirizine hydrochloride, clemastine fumarate, dexchlorpheniramine maleate, diphenylhydramine hydrochloride, azatadine maleate, diphenhydramine citrate, diphenhydramine hydrochloride, diphenylpyraline hydrochloride, doxylamine succinate, loratadine, promethazine hydrochloride, pyrilamine maleate, tripelennamine citrate, triprolidine hydrochloride, acrivastine, loratadine, desloratadine, brompheniramine, dexbrompheniramine, fexofenadine, cetirizine, montelukast sodium, related salts and the like;

(e) expectorants such as guaifenesin, ipecac, potassium iodide, terpin hydrate and the like;

(f) analgesic-antipyretics such salicylates, phenylbutazone, indomethacin, phenacetin and the like;

(g) antimigraine drugs such as sumitriptan succinate, zolmitriptan, valproic acid eletriptan hydrobromide and the like.

The amount of the additional API's in the formulation may be adjusted to deliver a predetermined dose of the active agent over a predetermined period of time, which may typically vary from 4 to 24 hours. Examples of doses containing specific pharmaceutically active agents are set forth in Table 1.

TABLE 1

| Pharmaceutically Active Agent | Dose |
|---|---|
| Chlorpheniramine Maleate | 4-12 mg |
| Brompheniramine Maleate | 4 mg |
| Dexchlorpheniramine | 2 mg |
| Dexbrompheniramine | 2 mg |
| Triprolidine Hydrochloride | 2.5 mg |
| Cetirizine | 5-10 mg |
| Acrivastine | 8 mg |
| Azatadine Maleate | 1 mg |
| Loratadine | 5-10 mg |
| Dextromethorphan Hydrobromide | 10-30 mg |
| Ketoprofen | 12.5-25 mg |
| Sumatriptan Succinate | 35-70 mg |
| Zolmitriptan | 2.5 mg |
| Nicotine | 1-15 mg |
| Diphenhydramine Hydrochloride | 12.5-25 mg |
| Atorvastatin | 5-80 mg |
| Valdecoxib | 5-20 mg |
| Celecoxib | 5-20 mg |
| Rofecoxib | 5-25 mg |
| Ziprasidone | 20-80 mg |
| Eletriptan | 10-40 mg |

Except as otherwise noted, the amount of API is designated as % by weight per dosage form. Generally, the amount of the API used may be from about 0.01% to about 80% by weight, or from about 0.1% to about 40% by weight, or from about 1% to about 30% by weight, or from about 1% to about 10% by weight.

An "effective" amount or a "therapeutically effective amount" of an active ingredient refers to a non-toxic but sufficient amount of the agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective" amount in any individual case can be determined by one of ordinary skill in the art using routine experimentation.

"Pharmacologically active" (or simply "active"), refers to a compound that has pharmacological activity and a "pharmacologically active" derivative of an active agent, refers to a derivative having the same type of pharmacological activity as the parent compound and approximately equal in degree. When the term "pharmaceutically acceptable" is used to refer to a derivative (e.g., a salt) of an active agent, it is to be understood that the compound is pharmacologically active as well. When the term "pharmaceutically acceptable" is used to refer to an excipient, it implies that the excipient has met the required standards of toxicological and manufacturing testing or that it is on the Inactive Ingredient Guide prepared by the Food and Drug Administration.

By "pharmaceutically acceptable" such as in the recitation of a "pharmaceutically acceptable excipient," or a "pharmaceutically acceptable additive," is meant a material that is not biologically or otherwise undesirable, i.e., the material can be incorporated into a pharmaceutical composition administered to a patient without causing any undesirable biological effects or interacting in a deleterious manner with any of the other components of the composition in which it is contained.

In various embodiments of the present invention, the dosage forms may be administered orally. Oral administration may involve swallowing, so that the composition with the API(s) enters the gastrointestinal tract, and/or buccal, lingual, or sublingual administration by which the API enters the blood stream directly from the mouth.

Formulations suitable for oral administration include solid, semi-solid and liquid systems such as tablets, soft or hard capsules containing multi- or nano-particulates, anhydrous liquids, or powders; lozenges (including liquid-filled); chewable tablets; fast disintegrating or fast dissolving tablets; gels; fast dispersing dosage forms; films; ovules; granules, wafers, gums, capsules, caplets, powders, sprays, and buccal/mucoadhesive patches. In one embodiment, a fast disintegrating dosage form is contemplated where a dry mixture of the components of the invention gives rise, upon direct compression, to fast disintegrating tablets having a disintegration time of less than about 60 seconds or less than about 30 seconds or less than about 15 seconds in the oral cavity.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. The compounds of the invention may also be used in fast-dissolving, fast-disintegrating dosage forms such as those described in Expert Opinion in Therapeutic Patents, 11 (6), 981-986, by Liang and Chen (2001).

Useful inactive ingredients, include but are limited to, binding agents, filling agents, lubricating agents, suspending agents, sweeteners, flavorings and flavor enhancer agents, taste-masking agents, preservatives, buffers, wetting agents, anti-oxidants, colorants or coloring agents, pharmaceutically acceptable carriers, disintegrants, plasticizers, salivary stimulating agents, cooling agents, co-solvents (including oils), pH adjusting agents, effervescent agents, emollients, bulking agents, anti-foaming agents, surfactants, soluble organic salts, permeabilizing agents, glidants and other excipients and combinations thereof. Desirably, the agents are chemically and physically compatible with the API.

Useful pH adjusting agents include fumaric acid, citric acid, malic acid, lactic acid, fumaric acid, glycolic acid and tartaric acid. Useful surfactants include sorbitan esters, docusate sodium, cetriride. Useful soluble organic salts include sodium chloride sodium phosphate, and potassium chloride.

Examples of useful binding agents include, but are not limited to, polyethylene glycols, soluble hydroxyalkylcelluloses, polyvinylpyrrolidone, gelatins, natural gums, various celluloses and cross-linked polyvinylpyrrolidone, microcrystalline cellulose, such as Avicel® PH101 and Avicel® PH102 and silicified microcrystalline cellulose such as ProSolv 50 and ProSolv 90.

Examples of useful substantially water soluble carriers or filling agents include, but are not limited to, various starches, celluloses, carbohydrates compression sugars, sugar alcohols, or soluble fillers. More particularly, useful fillers include but are not limited to, sucrose, mannitol, inositol, maltitol, sorbitol, lactitol, glucose, xylitol, erythritol, maltodextrins; microcrystalline cellulose, calcium carboxy methyl cellulose; pregelatinized starch, modified starches, potato starch, maize starch; clays, including kaolin and polyethylene glycols (PEG) including PEG 4000; or combinations thereof. Useful amount of fillers include the range of about 1 to about 99 weight percent, or about 25 to about 95 weight percent or about 40 weight percent to about 95 weight percent of the compositions of this invention.

Compositions of the present invention may include a sweetener. Useful sweeteners include, but are not limited to, sugars such as sucrose, glucose (corn syrup), dextrose, invert sugar, fructose, and mixtures thereof; acid saccharin and its various salts such as the sodium or calcium salt; cyclamic acid and its various salts such as the sodium salt; the dipeptide sweeteners such as aspartame and alitame; natural sweeteners such as dihydrochalcone compounds; glycyrrhizin; Stevia rebaudiana (Stevioside); sugar alcohols such as sorbitol, sorbitol syrup, mannitol, xylitol and the like, synthetic sweeteners such as acesulfame-K and sodium and calcium salts thereof and other synthetic sweeteners, hydrogenated starch hydrolysate (lycasin); protein based sweetening agents such as talin (thaumaoccous danielli) and/or any other pharmacologically acceptable sweetener known by the state of the art, and mixtures thereof.

Suitable sugar alcohols useful as sweeteners include, but are not limited to, sorbitol, xylitol, mannitol, galactitol, maltitol, isomalt (PALATINI™) and mixtures thereof. The exact amount of sugar alcohol employed is a matter of preference subject to such factors as the degree of cooling effect desired. Thus, the amount of sugar alcohol may be varied in order to obtain the result desired in the final product and such variations are within the capabilities of those skilled in the art without the need for undue experimentation.

In another embodiment, the formulations according to the invention are free of sugar. A sugar-free formulation has the advantage that it can be administered easily to consumers with blood sugar disorders or to diabetics in need of such preparations. High intensity sweeteners may be included in the formulation. Such sweeteners include, but are not limited to, sucralose, acesulfame potassium, and aspartame which share properties such as absence of bitter and metallic aftertastes.

In another embodiment, a composition may include acesulfame K, aspartame, sucralose and combinations thereof. Acesulfame K is a commercial product of Nutrinova Nutrition Specialties & Food Ingredient GmbH. Useful amounts of sucralose in a dosage form is between about 0.002% to about 10% by total weight of the FDDF. However, this amount can vary greatly depending upon the nature of the composition being sweetened. In one preferred embodiment, the sweetener is a mixture of sucralose with acesulfame K. The tablets may be uncoated, however, they can, if desired, be coated with any suitable coating agent known in the art. Suitable coating agents are those used for immediate release purposes and will disintegrate in saliva. Such coatings include, but are not limited to, hydroxypropyl methylcellulose, or methyl cellulose, or OPADRY™ and the like and combinations thereof.

Optionally, one or more flavors such as those described in U.S. Pat. No. 6,596,298 which is incorporated herein. Any amount of flavor can be used and will depend on characteristics of the active pharmaceutical ingredient(s); preferred concentration of flavoring is between about 0.01% to about 10% w/w of a composition. Flavors may include but are not limited to natural flavors, artificial flavors, volatile flavors, non-volatile flavors, cooling agents, warming agents and succulence agents.

A tablet disintegrant may be added to the direct compression process for its wicking (i.e., the ability of particles to draw water into the porous network of a tablet) and swelling ability. Some disintegrants also serve as excellent binders and are able to substantially improve the mechanical strength of the formulation. Suitable disintegrants are carboxymethyl cellulose sodium, crospovidone, corn starch, sodium starch glycolate, insoluble cationic-exchange resins such as polyacrylin, microcrystalline cellulose, silicified microcrystalline cellulose, croscarmellose. Disintegrants can be added at a concentration ranging from about 0.5% to about 30%. Croscarmellose sodium (cross-linked carboxymethyl cellulose) may be present at a concentration of about 2% to about 10%.

An effective amount of any generally accepted pharmaceutical tableting lubricant can be added to compress the tablets. An amount within the range from about 0.25% to about 6%, or 0.5% to about 3% by weight can be added. Useful tablet lubricants include, glyceryl monostearates, palmitic acid, talc, magnesium stearate, carnauba wax, polyoxyethylene monostearates, silicon dioxide, hydrogenated vegetable oils and fats, stearic acid and combinations thereof.

One or more glidant materials which improve the flow of the powder blend and minimize the dosage form weight variation can be used. Useful glidants include but are not limited to silicone dioxide, talc and combinations thereof.

The invention can further provide a taste-masked oral pharmaceutical composition including coating or encapsulating the systemically active therapeutic agent with a suitable coating material. Examples of suitable coating materials for taste-masking include polymers such as cellulose actetate, hydroxypropylmethylcellulose, ethylcellulose, hydroxypropylcellulose, methacrylates, methacrylate co-polymers such as Eudragit® (Butylmethacrylat-(2-Dimethylaminoethyl)methacrylat-Methylmethacrylat-Copolymer (1:2:1)"), KOLLICOAT®, and polyvinylpyrrolidone and mixtures thereof. The pharmaceutical composition can include other functional components presented for the purpose of modifying the physical, chemical or taste properties of the systemically active therapeutic agent. For example, the systemically active therapeutic agent can be in the form of fluid bed coated particles, microencapsulated particles, ion-exchange resin complex, such as a sulfonated polymers, electro-chemical melt, supercritical fluids, magnesium trisilicate, coacervation, or cyclodextrin (cyclic-linked oligosaccharides) complexes. Useful sulphonated polymers include polystyrene cross-linked with 8% of divinylbenzene such as Amberlite®IRP-69 and IRP-64 (obtained by Rohm and Haas), Dow XYS-40010.00®, Dow XYS40013.00® (obtained from the Dow Chemical Company).

The dose, pKa and solubility of the drug molecule influences formulation and taste masking methods. It is understood that any method in the art for masking the taste of pharmaceuticals to facilitate their oral administration can be used. For example, taste masking can also be achieved by simple wet granulation or roller compaction with other excipients to minimize presented surface area of the drug. Spray drying can also be used to taste mask the systemically active therapeutic agent.

It is further contemplated that the pharmaceutically active ingredients can be added in the form of an encapsulate. Encapsulation can be achieved using conventional procedures and can be performed using water-insoluble as well as water-soluble agents. Alternatively, it is possible to encapsulate a release controlling substance, together with the systemically active therapeutic agent, within an encapsulating shell to provide for controlled release of the taste-masked oral pharmaceutical composition.

An embodiment of the present invention provides for a process for preparing a tablet formulation. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Freeze or spray drying may also be used. The formulation of tablets is discussed in *Pharmaceutical Dosage Forms: Tablets*, Vol. 1, by H. Lieberman and L. Lachman (Marcel Dekker, New York, 1980).

Direct compression is a relatively quick process where the powdered materials are compressed directly without changing the physical and chemical properties of the drug. Direct compression excipients are chosen such that they have good flow and compressible characteristics and prevent segregation of powders in the hopper and thereby help in direct compression. For example, tablets may be obtained by blending together the spray dried API, and optional inactive ingredients, and optionally other therapeutically active ingredients and excipients to form a homogeneous mixture; blending together; and directly compressing the mixture.

In one particular embodiment phenylephrine is layered onto a substrate material. This may be employed using a process such as fluid bed layering or granulation. In order to perform this process the phenylephrine is dissolved or suspended into a layering solution with the optional addition of a binder, and sprayed onto a substrate particle, wherein the phenylephrine is dried or deposited on the surface of the particle. These materials may be dissolved or suspended in various solvents to produce the layering solution including but not limited to water, methanol, ethanol, isopropanol, acetone, and cyclohexane. Suitable substrate materials include but are not limited to compressible carbohydrates such as maltodextrin, mannitol, sorbitol, maltitol, xylitol, erythritol, lactitol, lactose, starch, starch derivatives and mixtures thereof, or cellulosic materials such as microcrystalline cellulose, silicified microcrystalline cellulose, and mixtures thereof. Suitable binders may include but are not limited to hydroxypropylcellulose, hydroxypropylmethylcellulose, starch, modified starch and mixtures thereof. The binder is present in the final layered particle, by weight of the final layered particle from about 0.1 percent to about 20 percent, e.g. about 0.1 percent to about 5 percent. The drug layering solution pH is adjusted using the addition of an organic acid such as citric acid, tartaric acid, malonic acid, ascorbic acid or fumaric acid or an inorganic acid such as phosphoric acid.

In one particular embodiment the pH of the drug layering solution is adjusted to a pH between about 4.5 and about 6.0, e.g. about 5.0. In another particular embodiment phenylephrine hydrochloride and chlorpheniramine maleate are added together to the drug layering solution. In one embodiment the ratio of phenylephrine hydrochloride to chlorpheniramine maleate is from about 5:1 to about 1:5, e.g. about 5:2 to about 2:5.

In another embodiment the pH may be adjusted using a base such as magnesium stearate, magnesium, hydroxide, calcium carbonate, aluminum hydroxide, magnesium hydroxide, sodium hydroxide, potassium hydroxide, or ammodium hydroxide. In another embodiment the layered particle is coated with a taste-masking polymer or combination of polymers or a sustained release polymer or combination of polymers. The average diameter of the substrate particle may be from about 30 to about 600 microns, or about 50 to about 400 microns. The average diameter of the particle following the layering step may be from about 40 microns to about 600 microns, or about 70 microns to about 400 microns.

Solid formulations for oral administration may be formulated to be immediate and/or modified controlled release. Controlled release formulations include modified release formulations include delayed-, sustained-, pulsed-, controlled-, targeted and programmed release.

Suitable modified release formulations for the purposes of the invention are described in U.S. Pat. No. 6,106,864, which is incorporated herein. Details of other suitable release technologies such as high energy dispersions and osmotic and coated particles are to be found in *Pharmaceutical Technology On-line*, 25(2), 1-14, by Verma et al (2001), which is incorporated herein. The use of chewing gum to achieve controlled release is described in WO 00/35298, which is incorporated herein.

Another embodiment of the present invention provides a kit having two or more separate compositions having a stabilized API and a means for separately retaining said compositions, such as a container, divided bottle, or divided foil packet. An example of such a kit is the familiar blister pack used for the packaging of tablets, capsules and the like. Other embodiments contemplate articles of manufacture including various packaging configurations, ranging from unit dose blister packs to multiple dose packages such as bottles. To assist compliance, the kit may have directions for administration and may be provided with a so-called memory aid.

In one embodiment, tablets are advantageously provided in blister packaging which is believed to limit the amount of oxygen that may interact with the composition containing the oxygen sensitive API and as such may also increase or enhance the stability of the drug product containing the oxygen sensitive API. Another embodiment contemplates a method of dispensing a composition from a blister pack by forcing the drug product through a foil back on a blister pack.

DRYING EXAMPLES

Example 1

| | |
|---|---|
| Phenylephrine HCl | 30 g |
| Citric Acid | 1 g |
| Maltodextrin | 120 g |
| Water | 200 g |

Example 2

| | |
|---|---|
| Phenylephrine HCl | 30 g |
| Malic Acid | 0.5 g |
| Maltitol | 150 g |
| Water | 350 g |

Example 3

| | |
|---|---|
| Phenylephrine HCl | 30 g |
| Lactic Acid | 1.5 g |
| Mannitol | 140 g |
| Water | 300 g |

Example 4

| | |
|---|---|
| Phenylephrine HCl | 30 g |
| Glycolic Acid | 1 g |
| Sorbitol | 200 g |
| Water | 200 g |

Example 5

| | |
|---|---|
| Phenylephrine HCl | 30 g |
| Tartaric Acid | 3 g |
| Xylitol | 180 g |
| Water | 300 g |

Example 6

| | |
|---|---|
| Phenylephrine HCl | 30 g |
| Citric Acid | 1 g |
| Lactitol | 175 g |
| Water | 500 g |

Example 7

| | |
|---|---|
| Phenylephrine HCl | 30 g |
| Tartaric Acid | 3 g |
| Erythritol | 150 g |
| Water | 300 g |

Example 8

| | |
|---|---|
| Phenylephrine HCl | 30 g |
| Citric Acid | 1 g |
| Xylitol | 200 g |
| Water | 400 g |

Example 9

| | |
|---|---|
| Phenylephrine Bitartrate | 46.8 g |
| Citric Acid | 1 g |
| Maltodextrin | 200 |
| Water | 400 |

Basic Process:
Phenylephrine HCl and polyol/support are dissolved in RT water. After complete solution, the acid is added, dissolved and then the solution dried. Spray drying with conditions appropriate to the equipment is the preferred means of drying. Other means of drying include evaporation in an oven and fluid bed drying.

Example 10

| | |
|---|---|
| Phenylephrine HCl | 30 g |
| Citric Acid | 1 g |
| Hydroxypropyl Cellulose | 2 g |
| Water | 400 g |

Phenylephrine HCL and hydroxypropyl cellulose are dissolved in RT water. After complete solution, the acid is added and dissolved in the solution. The solution is then sprayed onto silicified microcrystalline cellulose in an appropriate fluid bed granulator.

TABLET EXAMPLES

TABLE 2

| | Weight (mg/Tablet) Example # | | | | | |
|---|---|---|---|---|---|---|
| Ingredient | 1 | 2 | 3 | 4 | 5 | 6 |
| Spray Dried Phenylephrine HCl | 5.00 | 5.00 | 5.00 | 5.00 | 5.00 | 10.00 |
| Acetaminophen | | 325.00 | 325.00 | 325.00 | 325.00 | |
| Diphenhydramine HCl | | | 25.00 | 12.50 | | |

TABLE 2-continued

| Ingredient | Weight (mg/Tablet) Example # | | | | | |
|---|---|---|---|---|---|---|
| | 1 | 2 | 3 | 4 | 5 | 6 |
| Dextromethorphan HBr | | | | 20.00 | | |
| Guaifenesin | | | | | | 200.00 |
| Silicified Microcrystalline Cellulose (Prosolv 90) | 85.6 | 39.89 | 52.39 | 52.39 | 64.89 | 184.89 |
| Starch, pregelatinized, corn | 2.00 | 37.11 | 37.11 | 37.11 | 37.11 | 37.11 |
| Crospovidone USP/EP | 4.00 | 9.00 | 9.00 | 9.00 | 9.00 | 9.00 |
| Stearic acid NF Vegetable Source | 3.00 | 9.00 | 9.00 | 9.00 | 9.00 | 9.00 |
| Magnesium Stearate | 0.40 | | | | | |
| Acesulfame Potassium Salt | 0.152 | | | | | |
| Core weight | 100.152 | 450.00 | 450.00 | 457.50 | 450.00 | 450.00 |
| Blue Film Coating | | 13.50 | | | 13.50 | |
| Green Film Coating | | | 13.50 | | | |
| Yellow Film Coating | | | | 13.50 | | |
| White Film Coating | 6.08 | | | | | 13.50 |
| Wax, Candelilla | | 0.30 | 0.30 | 0.30 | 0.30 | 0.30 |
| Total weight | 106.232 | 463.80 | 463.80 | 471.30 | 463.80 | 463.80 |

Tablets with the formulation in Table 2 are prepared. Spray dried phenylephrine is transferred to a tote bin. The additional API's are added to the tote-bin. De-lumped crospovidone, starch and stearic acid is added to the tote bin and blended. De-lumped stearic acid and/or magnesium stearate is added to the tote bin and blended. The blended powder is compressed into a tablet by using a suitable tablet press. The coating material is dispersed in purified water and mixed. The cores as referenced to in Table 2 are loaded into a film coater and continuously sprayed with the coating. Acesulfame potassium salt in purified water is dissolved and Opadry II is dispersed and mixed to form a uniform and de-aerated suspension. This coating suspension is sprayed onto the tablets to attain a smooth and uniform film coating and a target weight of 4% of the white coated tablet weight.

The resulting tablets exhibit acceptable physical characteristics, such as look, color, hardness, etc. The resulting tablets have acceptable stability profiles.

Example 11

Chewable Tablets Containing Layered Phenylephrine Hydrochloride and Chlorpheniramine Maleate Particles Part A: Preparation of Phenylephrine (PHE) & Chlorpheniramine (CPM) Drug Layering Solution 500 mL of drug layering solution is prepared by dissolving 71.4 mg of phenylephrine hydrochloride, and 28.6 mg of chlorpheniramine maleate, 10.0 g hydroxypropylmethylcellulose 15 cps grade (Available from Dow Corp as Methocel E15) and 350 mL of deionized water. 50 mL of 0.75 mg/mL citric acid was added. The solution was adjusted to pH of 5.0 using 85% ammonium hydroxide solution.

Part B: Preparation of Layered Phenylephrine and Chlorpheniramine Layered Particles 1000 g of Microcrystalline Cellulose particles (Avicel PH200) crystals are added to a Glatt GPCG 1-3 fluid bed granulator fitted with a Wurster Insert. The drug layering solution from Part A is sprayed onto the microcrystalline cellulose at a spray rate of about 10 g/min under product temperature conditions of about 30° C. to about 34° C. and an atomization air pressure of 2.0 bar. The final layered particles contain about 6.43 percent phenylephrine hydrochloride and 2.58% chlorpheniramine maleate.

Part C: Production of Chewable Tablets for Evaluation Thereof

All materials set forth in Table 3 below (except the layered PHE and CPM particles) are manually passed through a 30 mesh screen. The resulting blend and the layered PHE and CPM particles are placed into a 4 quart V-Blender and mixed for 5 minutes.

TABLE 3

Components of Chewable Particles

| Ingredients | Percent (w/w) | mg/tab |
|---|---|---|
| Layered PHE and CPM Particles | 15.01 | 115.6* |
| Sucralose | 1.00 | 7.7 |
| Crospovidone | 0.52 | 4.0 |
| Orange Flavor | 1.10 | 8.5 |
| Stearic Acid | 0.80 | 6.2 |
| Mannitol Coarse Grade | 81.56 | 628.0 |
| TOTAL | 100.0 | 770.00 |

*Equivalent to 3 mg chlorpheniramine maleate and 7.5 mg phenylephrine hydrochloride.

The resulting blend is then removed from the blender and compressed on a rotary tablet press at 60 rpm using ½" round diameter flat faced beveled edge tablet tooling in order to yield tablets having a weight of 770 mg and a hardness range of about 4 to about 7 kiloponds as determined by the Hardness test set forth in Lieberman, and a thickness of about 5.4 to about 5.9 millimeters. At least 1500 tablets are prepared in accordance with this method.

While the invention has been described in detail and with reference to specific examples thereof, it will be apparent to one skilled in the art that various changes and modifications can be made therein without departing from the spirit and scope thereof of the invention.

What is claimed is:

1. A method of manufacturing a phenylephrine composition comprising:
    mixing phenylephrine and chlorpheniramine maleate into a drug layering solution; adjusting the pH of the solution to 4.5 to 6.0 by adding acid; layering said solution onto a substrate material, and drying said substrate material to form a solid formulation.

2. The method of claim 1, wherein said acid is selected form the group consisting of malic acid, fumaric acid, citric acid, phosphoric acid, lactic acid, glycolic acid, tartaric acid and mixtures thereof.

3. The method of claim 1, wherein said substrate material is selected from the group comprising maltodextrin, mannitol, sorbitol, maltitol, xylitol, erythritol, lactitol, lactose, starch, starch derivatives, microcrystalline cellulose and silicified microcrystalline cellulose.

4. The method of claim 1, wherein said phenylephrine is present in an amount from about 1 to about 60 milligrams.

5. The method of claim 4, wherein said phenylephrine is present in an amount from about 1 to about 15 milligrams.

6. The method of claim 5, wherein said phenylephrine is present in an amount from about 5 to about 12 milligrams.

7. The method of claim 1, wherein said chlorpheniramine maleate is present in an amount from about 0.25 to about 10 milligrams.

8. The method of claim 1, wherein said pH is about 5.0.

* * * * *